(12) United States Patent
McAllister et al.

(10) Patent No.: US 7,112,218 B2
(45) Date of Patent: Sep. 26, 2006

(54) TISSUE ENGINEERED BLOOD VESSELS AND APPARATUS FOR THEIR MANUFACTURE

(75) Inventors: Todd N. McAllister, San Diego, CA (US); Nicolas L'Heureux, San Diego, CA (US)

(73) Assignee: Cytograft Tissue Engineering, Inc., Novato, CA (US)

( * ) Notice: Subject to any disclaimer, the term of this patent is extended or adjusted under 35 U.S.C. 154(b) by 0 days.

(21) Appl. No.: 10/210,952

(22) Filed: Aug. 1, 2002

(65) Prior Publication Data
US 2002/0188349 A1    Dec. 12, 2002

Related U.S. Application Data

(62) Division of application No. 09/444,520, filed on Nov. 22, 1999, now Pat. No. 6,503,273.

(51) Int. Cl.
A61F 2/06    (2006.01)
C12M 1/00    (2006.01)

(52) U.S. Cl. ...................................... 623/1.41; 623/1.1

(58) Field of Classification Search ................. 623/1.1, 623/1.41, 1.44
See application file for complete search history.

(56) References Cited

U.S. PATENT DOCUMENTS

| | | | |
|---|---|---|---|
| 4,441,215 A | * | 4/1984 | Kaster ...................... 623/1.53 |
| 4,546,500 A | | 10/1985 | Bell |
| 5,618,718 A | | 4/1997 | Auger et al. |
| 5,628,786 A | | 5/1997 | Banas et al. |

OTHER PUBLICATIONS

"A Completely Biological Tissue-Engineered Human Blood Vessel," L'Heureux, N., et al., FASEB Journal, 12:47-56, Jan. 1998.*

* cited by examiner

*Primary Examiner*—Thomas Barrett
(74) *Attorney, Agent, or Firm*—Fish & Richardson P.C.

(57) ABSTRACT

The invention is a tissue engineered blood vessel (TEBV) made from a cultured fibroblast sheet rolled into a multilayer vessel which has sufficient burst strength to withstand physiological blood pressure without the inclusion of smooth muscle cells or synthetic scaffolding. The TEBV is made in a bioreactor having an enclosed chamber, a sheet growth module, a rollable mandrel, and a clamp for holding the sheet to the mandrel for rolling.

20 Claims, 3 Drawing Sheets

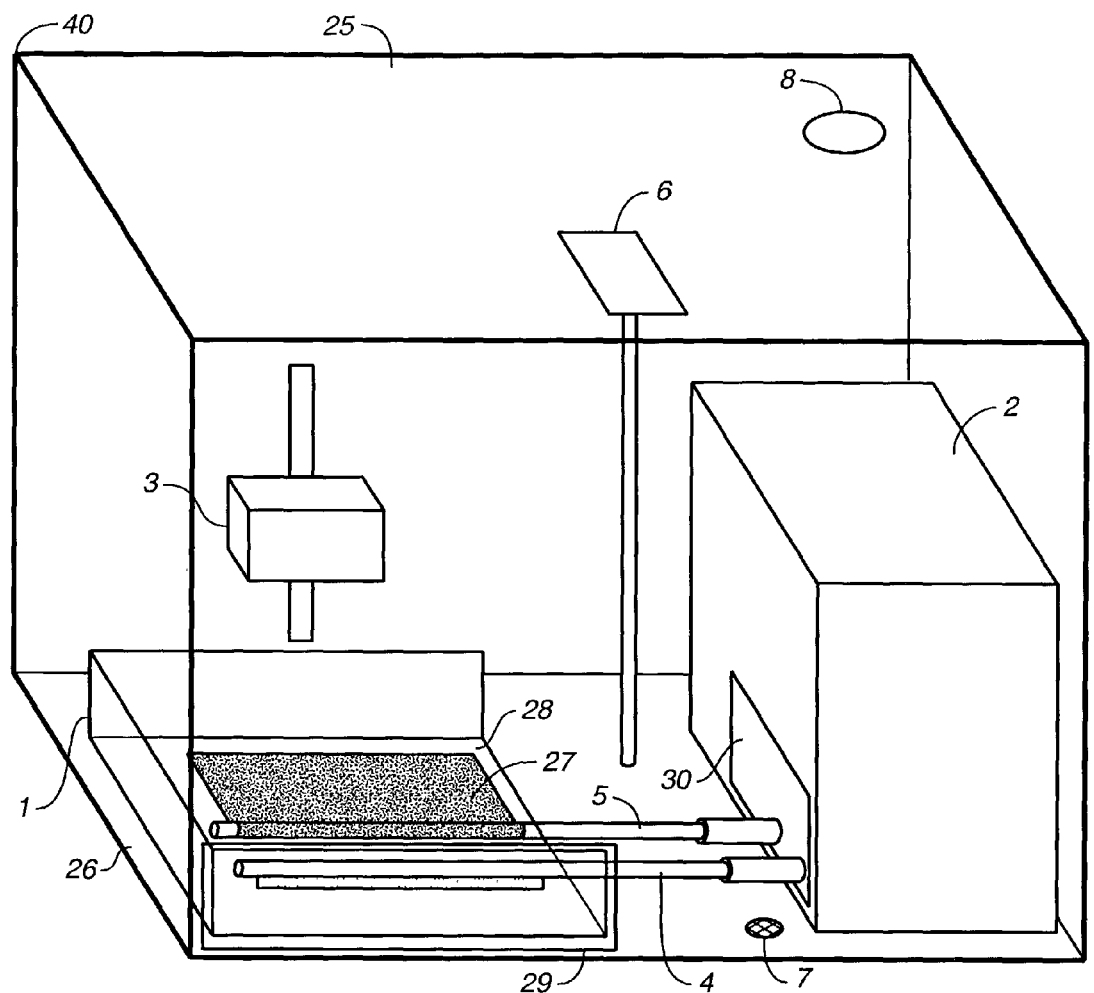
FIG._1
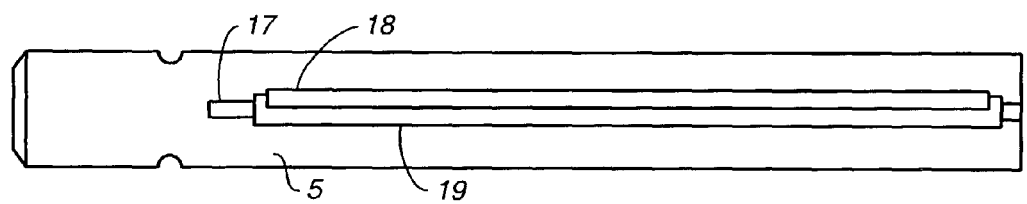
FIG._2a
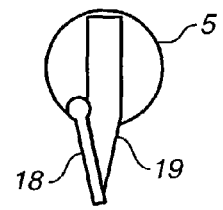
FIG._2b

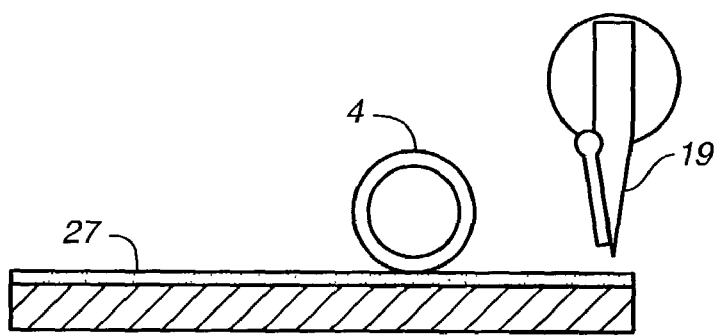
FIG._3a
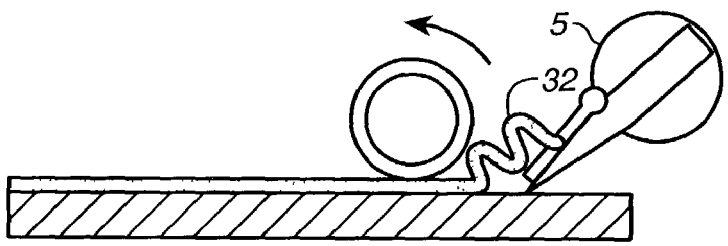
FIG._3b
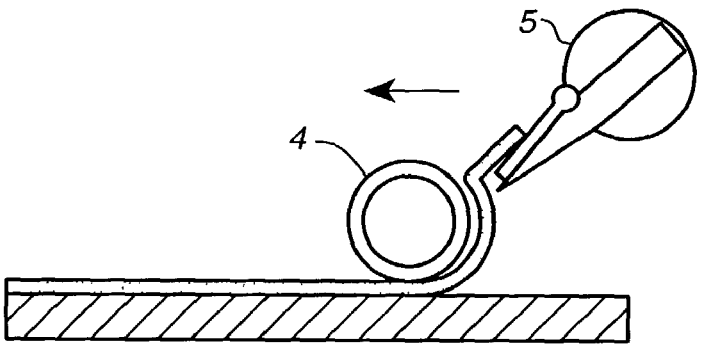
FIG._3c
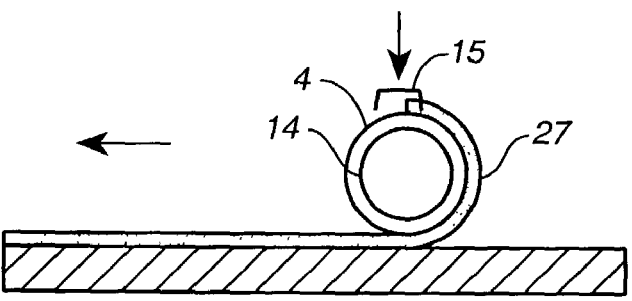
FIG._3d

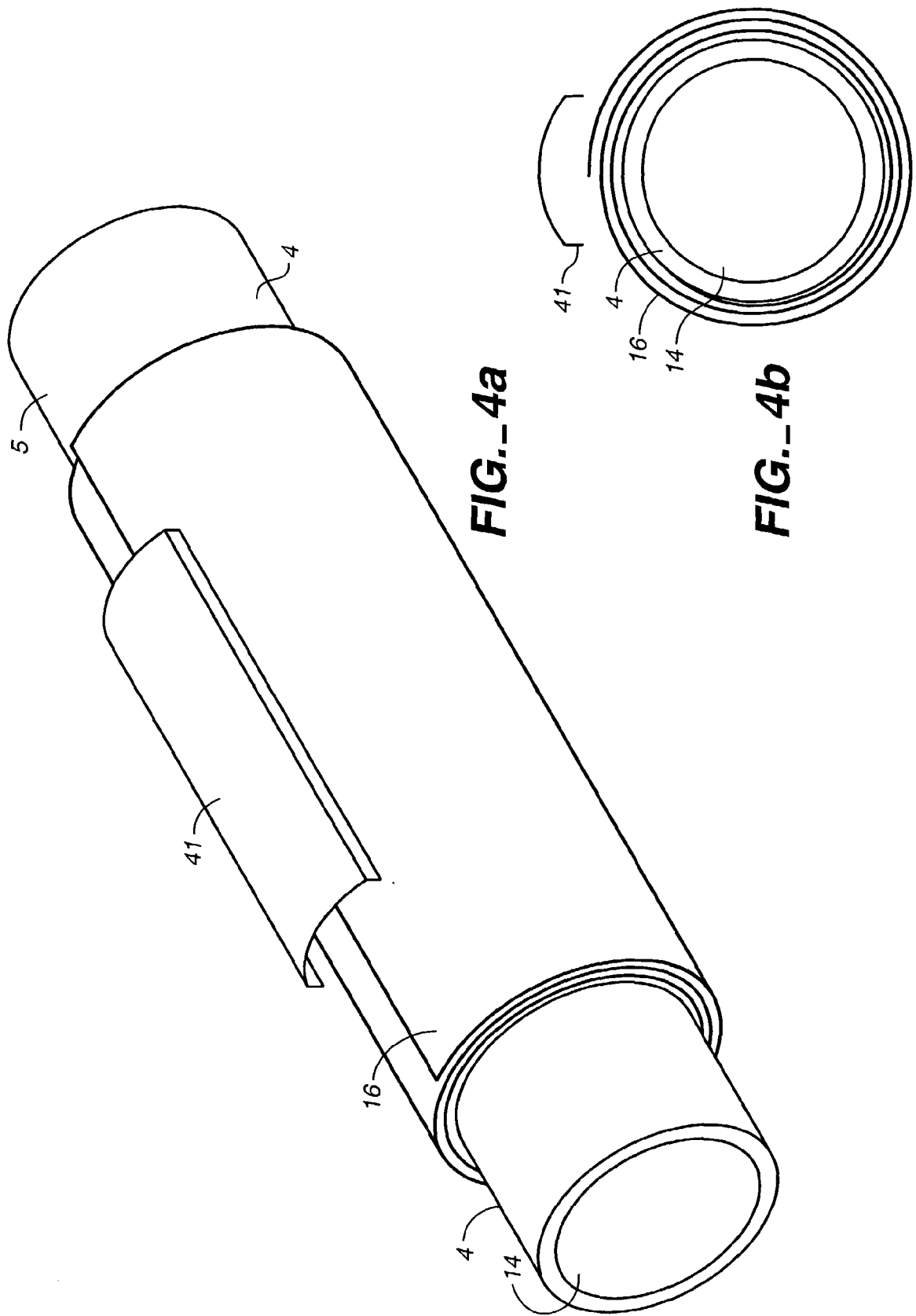
FIG._4a
FIG._4b

TISSUE ENGINEERED BLOOD VESSELS AND APPARATUS FOR THEIR MANUFACTURE

CROSS-REFERENCE

This application is a divisional application of and claims priority to U.S. application Ser. No. 09/444,520, filed on Nov. 22, 1999, now U.S. Pat. No. 6,503,273 the entire disclosure of which is incorporated by reference.

BACKGROUND AND PRIOR ART

This invention relates to a method and apparatus for the fabrication of autologous blood vessels without smooth muscle cells or non-biological scaffolding materials. The principal use of such blood vessels is for small diameter bypass grafts such as coronary artery bypass graft (CABGs), peripheral bypass grafts, or arteriovenous shunts.

Despite dramatic declines in the coronary heart disease related deaths over the last 30 years, heart disease remains the number one cause of death in the industrialized world. The decline in the death rate has coincided with the development and success of CABGs. In this procedure, vessels are typically harvested from the patient's own internal mammary arteries or saphenous veins (called an "autologous graft") and grafted into the coronary circulation to bypass arteries occluded by atherosclerotic plaques.

One important limitation of this procedure is that grafted vessels are susceptible to plaque regrowth leading to blockages (restenosis). Most CABGs using internal mammary arteries remain functional for 10–12 years. Beyond this timeframe, restenosis rates increase dramatically. Many patients therefore require a second bypass. In 1995, 573,000 grafts were performed in the U.S. alone, and 43% of these were in patients between 45 and 64 years of age, suggesting that a large fraction of these younger patients will live long enough to require a second procedure. However, due to previous vessel harvest or to vascular disease progression, suitable vessels for further arterial reconstruction often are not available. Currently, there is no clinically viable long-term treatment strategy for these patients. Over 50,000 Americans die annually due to the lack of graftable vessels. This number is likely to continue to rise, lagging 10 years behind the exponential growth in primary CABG procedures.

Prior attempts at finding alternate vessel sources focused on synthetic materials or dried and fixed tissue transplants. Larger diameter synthetic grafts have demonstrated reasonable functionality in the peripheral circulation. In the small diameter (less than 6 mm inside diameter) coronary circulation, however, synthetic grafts do not work and typically fail due to thrombogenesis (the formation of blood clots that occlude the vessel). Moreover, the synthetic materials often initiate chronic inflammatory responses that may be the cause of vessel failure.

In an effort to improve synthetic graft integration, synthetic biomaterials have been combined with autologous tissues from the patient. One procedure employs a tubular silicone mandrel surrounded by a Dacron mesh. This was implanted beneath the skin in patients scheduled for vascular reconstruction. After two months, the implant was removed from the patient and the Dacron mesh, along with a tightly integrated fibrous tissue, was slid away from the mandrel. This Dacron-supported scar tissue was then utilized as a vascular graft in the same patient. Although this graft combined autologous living cells and a natural extracellular matrix with a synthetic Dacron support, it still failed due to clotting.

Cell-seeded conduits have been tried that require resorbable, non-biological scaffolds to generate sufficient mechanical strength. In this approach, cells (typically smooth muscle cells) are seeded into tubular structures made from materials such as polylactic acid. These vessels are susceptible to the same thrombosis/inflammation failures associated with an immune response. It is also difficult to exactly match their biomaterial degradation rates with tissue remodeling. Vascular grafts made from synthetic materials also are prone to bacterial colonization and infection, which can result in loss of function or serious systemic complications.

Furthermore, these vessels provide no mechanism to limit the proliferation of smooth muscle cells. Smooth muscle proliferation may infiltrate the lumen of the vessel and occlude it in a process called intimal hyperplasia. Finally, synthetic grafts have very different mechanical properties from natural tissues. These differences, particularly in tissue compliance, may induce adverse remodeling responses and graft failure due to localized non-physiological hemodynamic forces.

One promising solution to the problems associated with synthetic-based vascular grafts is to assemble blood vessels in vitro using only the patient's own cells and then re-implant them into the patient. This approach is called tissue engineering. In theory, tissue-engineered blood vessels (TEBVs) should provide mechanically stable vessels built only from autologous tissue, therefore generating no immune responses. Another advantage to a tissue engineering approach is the ability to manipulate the vessel ends to facilitate grafting of the vessel into place. Tissue engineering has been used successfully in the past to build two-dimensional structures such as skin, but has had only limited success with three dimensional tissues and organs such as TEBVs. The most common problem with three-dimensional engineered tissues is a lack of structural integrity and mechanical strength. This is a particular problem for TEBVs, since these vessels will be subjected to significant mechanical loads both from blood pressure (which may be abnormally high in patients with heart disease), as well as relative motion between the anchoring sites of the vessel (the aorta and the myocardium). Moreover, the TEBVs must demonstrate sufficient suturability and tear-resistance to allow surgical handling and implantation.

Recently, a tissue engineering technique has been developed that is a radical departure from prior art techniques. This work is described in U.S. Pat. No. 5,618,718 and in an article entitled "A Completely Biological Tissue-Engineered Human Blood Vessel," L'Heureux, N., et al., FASEB J. 12:47–56, 1998, both of which are incorporated herein by reference. A fully biological and autologous human TEBV, with no synthetic materials, was made and found capable of withstanding physiological burst pressures in excess of 2000 mm Hg. These vessels were suturable and maintained patency for one week when xenografted into a dog. A living graft of this type is self-renewing with an inherent healing potential. The completely biological graft can be remodeled by the body according to the demands of the local mechanical environment. Moreover, the absence of synthetic materials precludes foreign body reactions, thus increasing the likelihood of long-term graft success.

These prior art TEBVs are prepared by rolling sheets of cultured fibroblasts and smooth muscle cells around a tubular mandrel. After a 2–8 week maturation period, the mandrel is removed and the vessel is seeded with endothelial cells. In this prior art procedure, the smooth muscle cells provide the TEBV with the ability to emulate a real blood vessel's ability to expand and contract. The smooth muscle cells also are responsible for the superior burst strength which in the past had been provided by the synthetic materials or scaffolds.

Even these prior art fully autologous TEBVs have significant problems. One of the biggest problems with TEBVs made from smooth muscle tissue is the difficulty associated with detaching and rolling the sheets of tissue while maintaining uniform vessel thickness. The inclusion of a smooth muscle layer complicates and lengthens the overall fabrication time by at least three weeks. Moreover, smooth muscle cells tend to uncontrollably proliferate. This undesired proliferation of cells may occlude the vessel. Moreover, the prior art rolling and tissue fabrication processes need to be improved and automated in order to obtain a clinically viable TEBV required for bypass grafts.

Contrary to the expectations in the art, a mechanically stable and fully autologous TEBV structure was discovered which could be fabricated without using smooth muscle tissue. The TEBV of this invention is made from fibroblasts and endothelial cells alone, thus eliminating the above-described problems caused by smooth muscle tissue. The new TEBV structure and method for its manufacture using an automated bioreactor are described below.

SUMMARY

This invention relates to a tissue engineered blood vessel (TEBV) made from a cultured fibroblast sheet rolled into a multilayer vessel which has sufficient burst strength to withstand physiological blood pressure without the inclusion of smooth muscle cells or synthetic scaffolding. The TEBV of the invention is made in the bioreactor of the invention having an enclosed chamber, a sheet growth module, a rollable mandrel and a clamp, preferably a magnetic clamp, for holding the sheet to the mandrel during rolling and maturation.

The process for making the TEBV of the invention begins with isolating and expanding fibroblasts from an autologous biopsy in a culture, producing a sheet of cells and extracellular matrix. The cell sheet is rolled onto a mandrel to produce a rolled vessel, which is then matured to make a TEBV.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 is a perspective view of the bioreactor of the invention, showing the chamber enclosure as transparent;

FIG. 2a is a side view of the detaching mandrel of the invention;

FIG. 2b is a cross-section of the detaching mandrel of FIG. 2a;

FIGS. 3a, 3b, 3c, and 3d are cross-sectional views which show the tissue rolling process of the invention; and FIGS. 4a and 4b are perspective and cross-sectional views, respectively, of the TEBV of the invention rolled on a mandrel.

DETAILED DESCRIPTION

The first step in the process of making the TEBV of this invention is to prepare a sheet of fibroblasts. This sheet includes fibroblasts taken from the patient's own body (an autologous graft) or from donor tissue (an allograft). Allograft tissues have the advantage of being able to treat many patients from a single donor source. However the cells used in allograft tissue must be treated to eliminate physiological foreign body responses. This treatment typically includes removing surface antigens such that host antibodies cannot label the cells for destruction. This can be accomplished chemically or enzymatically.

In a preferred embodiment of the invention, autologous cells are harvested from the patient's own body to eliminate the risks of disease transmission and tissue rejection. Nearly all tissue biopsies contain some endothelial cells and some fibroblasts. Therefore, almost any biopsy procedure or tissue harvest will provide a suitable starting point for both. Skin or blood vessels are the best tissue sources.

The skin biopsy is accomplished, as is well known in the art, by harvesting from a patient a small patch of skin and fat, and then isolating the endothelial cells from the capillaries and the fibroblasts from the dermis. Blood vessel biopsies can be taken by removing a small segment of a peripheral vein or artery, preferably a jugular vein (or similar superficial vessel). Alternatively, a small segment can be harvested endoscopically (via a catheter) or by dissecting out a deep vessel. Mesothelial cells harvested from fat can be used in place of endothelial cells.

Once a suitable biopsy is taken, fibroblasts must be isolated and expanded to obtain purified cultures. However, reasonably low levels of other cell types may exist in the purified cultures. Fibroblasts can be isolated from the biopsy by several different well-known techniques. The easiest is manual dissection of skin or blood vessels to separate the fibroblast-containing tissue. For skin biopsies, the dermis must be isolated, taking care to remove hair follicles which are a source of keratinocyte contamination. For blood vessel biopsies, the adventitia must be isolated from the media and endothelial layers. Fibroblasts can be harvested from this portion of the tissue explant by cell outgrowth or by enzymatically digesting the explant and plating the digested tissue.

Fibroblasts can also be isolated by varying the culture conditions to favor their growth. Surface material choice (glass versus plastic) or surface preparation (gelatin or fibronectin coating) can be selected to favor fibroblast proliferation. Likewise, media additives and pH can be adjusted to promote a preference for endothelial cell or fibroblast proliferation. After a few passages, the cell population will be sufficiently pure. Fibroblasts may also be isolated by flow cytometry. In practice, fibroblasts are more difficult to sort by this technique, as there are no clear antibodies that are unique to fibroblasts.

After the fibroblasts have been isolated, they must be cultured and grown into sheets with sufficient mechanical strength to be detached and rolled into three-dimensional conduits. Mature sheets of fibroblasts and their extracellular matrix proteins typically take approximately four weeks to produce, but this time depends upon initial seeding density, media characteristics, and surface preparation. There is some variability between patients as well. Additional cells can be added to the fibroblasts at any stage of sheet formation. These cells can include additional human or animal cells or transfected or otherwise genetically modified cells.

Referring to FIG. 1, sheet growth, detachment, and rolling to make the TEBV are accomplished in bioreactor 40 of this invention. This bioreactor is designed specifically for fabrication of TEBVs. Prior art cell culture bioreactors are for the most part designed for cell suspensions of non-adherent cells or for expansion of cell monolayers. Therefore they do not provide the means of detaching and rolling adherent sheets of tissue required for the TEBVs of this invention.

Sheet growth is carried out in sheet growth module 1 located within chamber 25 of bioreactor 40. Module 1 may have a lid (not shown). Bioreactor 40 includes automated motion control devices 2 and 3 to facilitate sheet detachment and rolling, and lid removal, respectively. During sheet formation, non-fibroblast cellular contaminants are minimized, and cells are stimulated to produce a robust extracellular matrix (ECM). Inducing the formation of an ECM is a critical component of a fully biological TEBV. There are several ways to stimulate production of ECM proteins. In the preferred embodiment, media constituents, such as ascorbic acid, are added to stimulate ECM production. Substrate 26 of module 1 preferably has a sterile polystyrene surface that has been electrostatically treated and coated with a protein, such as gelatin or fibronectin, to promote cell adhesion. Other surfaces for substrate 26, including glass, acrylic or metal such as titanium, can be used instead of polystyrene.

Media and gas exchange in chamber 25 is controlled automatically. Chamber 25 includes a one-way valve 8 designed to preserve the sterility within chamber 25 and a drain 7 to remove fluids from chamber 25. Media and gas can be metered into and out of chamber 25 through valve 8. The sheets 27 are maintained in a constant environment throughout the cell expansion phase. Fibroblasts are seeded into the sheet growth process in the chamber 25 at an initial density of approximately 10,000 cells per $cm^2$, although seeding density is not critical to the invention.

After seeding, the first maturation and proliferation phase of the sheet growth begins. Fibroblasts will proliferate in almost any serum-containing cell culture media. A preferred media to optimize the fibroblast proliferation rate and the production of extracellular matrix proteins (which provide mechanical strength to the sheet) is DMEM and Hams F12 in a 1:1 ratio, supplemented with 10% fetal calf serum and antibiotics. A preferred embodiment also includes ascorbic acid or other ascorbate derivatives because they accelerate the production of the extracellular matrix proteins.

There are several growth conditions that must be maintained during sheet growth in module 1. First, the media pH should be maintained in a range between about 5 and 9, preferably approximately 7.4. Second, the media temperature should be maintained in a range between about 25° C. and 45° C., preferably approximately 37° C. Third, a sterile air environment should be employed, preferably including up to 20% $CO_2$. In addition, an adequate media exchange rate must be maintained to prevent exhausting critical media constituents.

Bioreactor 40 can be expanded to allow multiple sheets simultaneously to be fed from one reservoir using multiple modules 1 (only one is shown). Each patient's cells will mature in a separate module fed by a common media source through valve 8. The modules may be isolated from each other and from the common reservoir by sterile filters and interconnected passages controlled by solenoid valves (none of which is shown). Alternatively, module 1 can be removed from bioreactor 40 and stored in a separate incubator (not shown). Module 1 includes one-way valves (not shown) to exchange media and gases from a common reservoir. The rate of media exchange can be varied between continual and weekly exchange, but typically between about 25%–100% of the media is exchanged each day, preferably about 50% being changed every two days.

Referring to FIGS. 1 and 2, sheet growth and maturation module 1 of this invention is adapted for the automated rolling steps using an automated rolling device to roll the TEBVs. Sheets 27 remain in module 1, which is designed to be inserted into the bioreactor from port 29 at the front, as shown. The lid (not shown) and one side 28 of module 1 are removable to allow the rolling mandrel 4 and control rod 5 to rest on sheet 27. Alternatively, side 28 may have apertures for the mandrel and rod. As shown in FIGS. 2a and 2b, a preferred embodiment of control rod 5 consists of a bladed mandrel with a foam backing.

The rods used for each step are inserted into motion control device 2 from the left side. A cartridge 6 of rolling mandrels and/or control rods can be accessed without human intervention by the motion control device 2. When a patient's sheet expansion module is inserted into the bioreactor 40, a sterile set of control rods and/or mandrels 6 is hung from the top of the chamber 25, as shown. The motion control device 2 can move in three dimensions to access a new mandrel or control rod from cartridge 6. Control rod 5 preferably has a slot 17 for attachment of various tools. Other options to access and roll the sheet may be employed that may necessitate additional gearing between the motion control device and the mandrel.

Referring to FIGS. 1, 2a, 2b, and 3a–3d, the first tool used to initially separate leading edge 32 of the tissue layer to be rolled from the underlying cell substrate is control rod 5 with rubber blade 19 attached to it along its length, as shown in cross-section in FIG. 2b. Blade 19 is rotated against the tissue sheet 27 in a manner to separate about 1–3 cm of the leading edge 32 of tissue as shown in FIG. 3b. After separation, leading edge 32 will float slightly and be capable of being lifted and draped over mandrel 4, as shown in FIG. 3c. The preferred mandrel 4 has a surface of Teflon or other material which does not allow significant cell adhesion. Alternatively, the surface of mandrel 4 can be a biological material, biodegradable synthetic compound or biologically active compound.

Referring to FIGS. 2a, 2b, and 3a–3d, the next step is to begin rolling sheet 27 around mandrel 4. To facilitate this rolling, a second tool, for example, sponge 18 mounted on control rod 5 as shown in FIG. 2b, is rotated in contact with the separated edge 32 of tissue sheet 27 as shown in FIG. 3b. This rotation transfers the edge 32 of the tissue to mandrel 4 about which the tissue will be rolled. Once the tissue has been draped over the mandrel 4, as shown in FIG. 3c, it can be clamped onto mandrel 4 using clamp 15 as shown in FIG. 3d to facilitate the rolling process.

There are a variety of clamping techniques that may be used. A preferred embodiment shown in FIGS. 4a and 4b employs a metal clamp 15. Briefly, in accordance with this invention, a magnetic core 14 is inserted into the inside of mandrel 4 so that the metallic clamp 15 (shown in FIG. 3d) can be held onto mandrel 4 by the field of magnetic core 14. This clamping force can be varied by altering the size of the magnet which is used for core 14, the number of magnets used, the strength of the magnets, the separation distance between the core 14 and clamp 15, the ferrous content of clamp 15 or the material used for mandrel 4. In a preferred embodiment, the magnetic strength of core 14 can be varied externally, using methods well known in the art. For example, a magnetic field may be induced in an iron-containing core by applying a current through a coil (not shown) wrapped around core 14. By changing the magnitude of the applied current, the magnetic field can be increased or decreased proportionally.

Other clamping devices can be utilized for clamp 15, such as a mechanical clamp, biological adhesives (fibrin glue) or a slot in the mandrel itself, as will be described below. Mechanical clamps can be added to the edges or across the long axis of mandrel 4 that will use spring force or other type of fastening to secure the rolled tissue 1 to the mandrel.

Different protein coatings can also be utilized to increase the friction between the mandrel and tissue. This "glue" can later be solubolized or denatured chemically, enzymatically, acoustically, or thermodynamically. Where the mandrel has a longitudinal slot 17 shown in FIG. 2a, the leading edge 32 (FIG. 3b) of the tissue can be dropped into slot 17. The tissue is then held in place by the spring force of mandrel 4, or by inserting the leading edge 32 into a core (not shown) that secures the sheet to the inner surface of mandrel 4.

Mandrel 4 with sheet 27 firmly attached by clamp 15, as shown in FIG. 3d, is then rotated and translated to wind the tissue 16 around it as shown in FIGS. 4a and 4b. Motion control device 2 is used to maintain uniform tension and tissue thickness during rolling. The elimination of bubbles and tension inconsistencies contributes to increased strength of the TEBV.

The ends of the mandrel 4 do not have to be cylindrical. They may be flared or tapered to facilitate grafting. Staples or sutures may also be placed into the TEBV ends to further simplify surgical handling of the TEBVs.

The TEBV can be made with or without an internal membrane. In the preferred embodiment, an internal membrane is used, made of a sheet of fibroblasts that has been air dried to generate dead fibroblasts or otherwise kill the fibroblasts or denatured (decellularized). After rolling has been completed, the internal membrane and outer fibroblast plies can be converted from a single sheet of fibroblast by selectively killing or denaturing the inner layers by several well-known techniques, including thermal shock, ultrasound, preventing or limiting media or gas exchange on the inner surface, or releasing a localized toxin at the inner surface.

After rolling, clamp 15, which remains inside the roll, can be left in place or removed. Another clamp 41, shown in FIG. 4a, may be placed around the rolled vessel, using any one of the means described above to prevent unwinding.

Next the rolled vessel is transferred to a second module for the maturation phase. This module frees up chamber 25 for rolling other TEBVs. This maturation phase will last about eight weeks, although shorter or longer periods are possible. The sequentially applied layers of the TEBV fuse together during this phase, forming a homogenous TEBV.

There are at least two possible types of maturation reactors. The simplest is a passive reactor similar to module 1, which exchanges media in the manner described in the sheet formation phase. The disadvantage of such a reactor is that vessel thickness is limited by diffusion. Thicker tissues and faster maturation can be generated by using a module of a preferred embodiment of the invention which applies a pressure differential across the vessel wall. Negative pressure in the mandrel core is preferred. Placing small perforations in the mandrel, or using a porous material for the mandrel will keep the vessel collapsed against the mandrel support. Positive pressure can also be used. Applying a pressure gradient across the vessel wall not only increases mass transport, but also will enhance interstitial fluid flow, thereby stimulating the cells and increasing the mechanical strength of the TEBV.

When the maturation phase is complete, the mandrel 4 is removed and the vessels are cannulated to introduce endothelial cells. These cells are isolated in a manner similar to fibroblasts. First, the endothelium is separated from a harvested blood vessel using mechanical force (gently scraping the lining of the vessel) or, in a preferred embodiment, using enzymatic digestion. Collagenase, for example, will preferentially release the endothelium. Vessels are exposed to an enzyme (collagenase, for example) such that the endothelial layer is preferentially released.

Isolating endothelial cells from skin samples or other tissue samples is more difficult than isolating fibroblasts, but can be done by controlling the culture conditions to favor endothelial cell attachment and proliferation or by immunological techniques, as is known in the art. Immunological techniques require cell-specific antibodies such that the cells of interest (or everything but the cells of interest) are labeled. Antibody-tagged cells can then be sorted by flow cytometry. In this technique, a fluorescent marker is coupled to the antibody so that cells marked by that antibody fluoresce and can be sorted from non-fluorescing cells.

After sufficiently pure cultures of endothelial cells are obtained, the cells must be expanded to provide enough cells to seed the lumen of the TEBV. Endothelial cells may lose important phenotypic characteristics after multiple passages. It is therefore important to maximize the initial harvest such that in vitro expansion is minimized.

After a sufficient quantity of endothelial cells has been obtained, the cells are detached (typically by enzymatic or mechanical means) and placed into a suspension. The suspension is introduced into the lumen of the TEBV via a cannula. After seeding with endothelial cells, the cannula is removed and the TEBV is left in the maturation chamber to allow the endothelium to grow to confluence and anchor securely to the biological substrate. The resultant TEBVs can be grafted in the patient at this point or, if desired, the inner lining of the vessels may be further conditioned using hemodynamic forces by introducing fluid flow down the cannula and through the vessel.

It is preferable to use the TEBVs soon after the endothelial layer reaches confluence because it is difficult to maintain endothelial cells in a serum-containing culture for long periods of time. However, in some cases, the vessels may be removed from the maturation module and preserved by freezing, freeze-drying, or preserved by other means.

As will be understood by those skilled in the art, many changes in the apparatus described above may be made by the skilled practitioner without departing from the spirit and scope of the invention, which should be limited only as set forth in the claims which follow.

What is claimed is:

1. A TEBV consisting of:
   a) an inner layer of endothelial cells;
   b) a middle layer of denatured fibroblasts; and
   c) an outer layer of living fibroblasts.

2. The TEBV of claim 1 which is prepared as follows:
   a) providing a first fibroblast layer which is a cultured fibroblast sheet rolled into a multilayer vessel which has been matured and then denatured;
   b) rolling a cultured fibroblast sheet around the first fibroblast layer to form a second fibroblast layer;
   c) maturing the second fibroblast layer; and
   d) forming a layer of endothelial cells on the inner surface of the first fibroblast layer.

3. The TEBV of claim 1 wherein the fibroblasts are stimulated to produce an extracellular matrix (ECM).

4. The TEBV of claim 1 wherein the fibroblasts are autologous.

5. The TEBV of claim 1 wherein the fibroblasts are allogenic.

6. The TEBV of claim 1 wherein the fibroblasts are genetically modified.

7. The TEBV of claim 1 wherein the endothelial cells are autologous.

8. The TEBV of claim 1 having two ends adapted to be attached to a human blood vessel.

9. The TEBV of claim 8 wherein staples are attached to one end.

10. The TEBV of claim 8 wherein sutures are attached to one end.

11. The TEBV of claim 8 wherein sutures are attached to both ends of the TEBV.

12. The TEBV of claim 8 wherein staples are attached to both ends of the TEBV.

13. The TEBV of claim 8 wherein the ends are tapered.

14. The TEBV of claim 4, wherein the autologous fibroblasts are obtained from a subject having a vascular disease.

15. The TEBV of claim 11 wherein the two ends are flared.

16. The TEBV of claim 1 wherein the fibroblasts are obtained from skin or a blood vessel.

17. The TEBV of claim 1 wherein the endothelial cells are obtained from skin or a blood vessel.

18. The TEBV of claim 1 wherein at least one fibroblast layer is matured after rolling.

19. The TEBV of claim 1 which is prepared by rolling a cultured fibroblast sheet into a multilayer vessel, selectively denaturing at least one inner layer of the vessel and forming a layer of endothelial cells on the inner surface of the denatured fibroblast layer.

20. The TEBV of 19 wherein the rolled fibroblast sheet is matured prior to denaturation.

* * * * *